United States Patent
Bessette et al.

(10) Patent No.: US 6,812,258 B2
(45) Date of Patent: Nov. 2, 2004

(54) CANCER TREATMENT COMPOSITION AND METHOD USING NATURAL PLANT ESSENTIAL OILS

(75) Inventors: Steven M. Bessette, Brentwood, TN (US); Essam E. Enan, Franklin, TN (US)

(73) Assignee: Ecosmart Technologies, Inc., Franklin, TN (US)

( * ) Notice: Subject to any disclaimer, the term of this patent is extended or adjusted under 35 U.S.C. 154(b) by 232 days.

(21) Appl. No.: 10/190,667

(22) Filed: Jul. 9, 2002

(65) Prior Publication Data

US 2003/0017218 A1 Jan. 23, 2003

Related U.S. Application Data

(62) Division of application No. 09/455,542, filed on Dec. 7, 1999.
(60) Provisional application No. 60/111,271, filed on Dec. 7, 1998.

(51) Int. Cl.$^7$ ........................................... A61K 31/7075
(52) U.S. Cl. ....................................... 514/720; 424/725
(58) Field of Search ......................... 514/720; 424/725

(56) References Cited

U.S. PATENT DOCUMENTS

| | | | |
|---|---|---|---|
| 5,595,756 A | 1/1997 | Bally et al. | |
| 5,626,854 A | 5/1997 | Ichii et al. | |
| 6,028,061 A | 2/2000 | Bernfield et al. | |

FOREIGN PATENT DOCUMENTS

| | | |
|---|---|---|
| DE | 3515253 | 6/1986 |
| DE | 3829200 | 3/1990 |
| EP | 0264660 | 4/1988 |
| FR | 2697133 | 4/1994 |
| FR | 2 706 771 | 12/1994 |
| GB | 2 151 924 | 7/1985 |
| JP | 357106697 | * 7/1982 |
| JP | 3263481 | * 11/1991 |
| WO | WO9311775 | 6/1993 |
| WO | WO9948469 | 9/1999 |
| WO | WO0024409 | 5/2000 |
| WO | WO0025802 | 5/2000 |
| WO | WO9948386 | 8/2003 |

OTHER PUBLICATIONS

Ito et al "Proceedings of the Intern Cancer Cong,Plenary and Special Lect 16$^{th}$" pp. 159–164 Oct. 30 Nov. 5, 1994.*
Berthois, Y., Katzenellenbogen, J., and Katzenellenbogen, B., "Phenol red in tissue culture media is a weak estrogen: Implications concerning the study of estrogen–responsive cells in culture" Proc. Natl. Acad. Sci. vol. 83: 2496–2500. Apr. 1986.
Davis, D., Bradlow, H., Wolff, M., Woodruff, T., Hoel, D., and Anton–Culver, H., "Medical Hypothesis: Xenoestrogens As Preventable Causes of Breast Cancer" Env. Health Per. 101(5):372–377. Oct. 1993.
Dees, C., Foster, J., Ahamed, S., and Wimalasena, J., "Dietary Estrogens Stimulate Human Breast Cells to Enter the Cell Cycle" Environ. Health Perspect. 105(Suppi 3):633–636. Apr. 1997.
Dewailly, E., Dodin, S., Verreault, R., Ayotte, P., Sauve, L., Morin, J. and Brisson, J., "High Organochlorine Body Burden in Women With Estrogen Receptor–Positive Breast Cancer" J. Nati. Cancer Inst. 86(3):232–234.
Harris, J., Lippman, M., Veronesi, U., and Willett, W., "Breast Cancer" New England J. of Med. 327(5):319–328. 1992.
Henderson, B., Ross, R., and Pike, M., "Hormonal Chemo-prevention of Cancer in Women" Science 259–633–638. 1993.
Hoffman, M., "New Clue Found to Oncogene's Role in Breast Cancer" Science 256:1129. 1992.
Jobling, S., Reynolds, T., White, R., Parker, M., and Sumpter, J., "A Variety of Environmental Persistent Chemicals Including Some Phthalate Plasticizers, Are Weakly Estrogenic" Envir. Health. Per. 103:582–587. 1995.
Miller, F., Soule, H., Tait, L., Pauley, R., Wolman. S., Dawson, P., and Heppner, G., "Xenograft Model of Progressive Human Proliferative Breast Disease" J. Natl. Cancer Inst. 85(21):1725–1731. 1993.
Mussalo–Rauhamaa, H., Hasanan, E., Pyysalo, H., Antervo, K., Kauppila, R., and Pantzar, P. "Occurrence of Beta–Hexachlorocyclohexane in Breast Cancer Patients" Cancer. 66:2124–2128. 1990.
Nelson, J., Struck, R., and James, R., "Estrogenic Activities of Chlorinated Hydrocarbons" J. Tox. Envir. Health 4:325–339. 1978.
Osborne, C. K., Hamilton, B., Nover, M., and Ziegler, J., "Antagonism between Epidermal Growth Factor and Phorbol Ester Tumor Promoters in Human Breast Cancer Cells" J. Clin. Invest. 67:943–951. 1981.
Reese, J., and Katzenellenboge4n, B., "Differential DNA–binding abilities of estrogen receptor occupied with two classes of antiestrogens: studies using human estrogen receptor overexpressed in mammalian cells" Nucleic Acids Res. 19(23):6595–6602. 1991.
Soto, A. M. and Sonnenschien, C., "The Role of Estrogens on the Proliferation of Human Breast Tumor Cells (MCF–7)" J. Steroid Biochem. 23(1):87–94. 1985.
Wolff, M., Toniolo, P., Lee. E., Rivera, M., and Dubin, N., "Blood Levels of Organochlorine Residues and Risk of Breast Cancer" J. Natl. Cancer Inst. 85(8): 648–652. 1993.
Ciardiello, Fortunato and Tortora, Giampaolo, "Interactions between the Epidermal Growth Factor Receptor and Type I Protein Kinase A: Biological Significance and Therapeutic Implications", Clinical Cancer Research, vol. 4, pp. 821–828. Apr. 1998.

(List continued on next page.)

Primary Examiner—Herbert J. Lilling
(74) Attorney, Agent, or Firm—Nixon & Vanderhye P.C.

(57) ABSTRACT

Pharmaceutical compositions containing plant essential oils, natural or synthetic, or mixtures or derivatives thereof, for the prevention and treatment of soft tissue cancer in mammals.

3 Claims, No Drawings

OTHER PUBLICATIONS

Computer Caplus Abstrct Kim et al. 1998:101607 "Antianaphylactic Properties of Eugenol" Pharma Res. (1997) 36(6) 475–480.

Computer Caplus Abstract Oieta et al. 1985:427328 "Ophthalmic Pharmaceutical" R084026.

Computer Caplus Abstract German 3829200 "Eugenol–Isoeugenol Mixtures for Treatment of Aids" 1988.

Computer Caplus Abstract Luc et al. 1993:168134 "Bactericidal Pharmaceutical Composition Containing Chlorhexidine and Euegenol" 1993.

Sylvie Bardon, et al., Monoterpenes Inhibit Cell Growth, Cell cycle Progression, and Cyclin D1 Gene Expression in Human Breast Cancer Cell Lines, Nutrition and Cancer, vol. 32, No. 1, 1998, pp. 1–7.

Clardiello et al. "Interactions Between the Epidermal Growth Factor Receptor and Type I Protein Kinase A: Biological Significance and Therapeutic Implications" Clinical Cancer Research vol. 4, pp. 821–828.

Yokota et al. "Suppressed Mutagenicity of Benzo[A]Pyrene by the Liver S9 Fraction and Microsomes from Eugenol–Treated Rats"; Mutation Research, 172 pp. 231–236.

* cited by examiner

CANCER TREATMENT COMPOSITION AND METHOD USING NATURAL PLANT ESSENTIAL OILS

CROSS REFERENCE TO RELATED APPLICATION

This application is a divisional based from U.S. patent application No. 09/455,542 filed on Dec. 7, 1999 which claims the benefit of U.S. Provisional Patent Application No. 60/111,271, filed Dec. 7, 1998, the entire disclosures of which are incorporated herein by reference.

FIELD OF THE INVENTION

The present invention relates, in general, to therapeutically effective pharmaceutical compositions containing plant essential oil compounds, and methods for using same for prophylactically or therapeutically treating of soft tissue cancers in mammals, including humans, such as, for example, breast cancer.

BACKGROUND OF THE INVENTION

Breast cancer is a proliferative disease of mammary epithelial cells and estrogen has been shown to stimulate cell proliferation of these cells both in culture and in mice (Soto and Sonnenschein, 1985; Osborne, 1981). Xenoestrogens have been proposed to stimulate cell proliferation through binding and activating estrogen receptors (ERs) (Miller et al., 1993; Hoffman, 1992). The incidence of breast cancer has been steadily rising during the past two or three decades, a trend characterized by increasing rates among estrogen-responsive tumors, by continuing increases among older women, and by growing numbers in both developed and developing countries (Harris et al., 1992). Between 1973–1980, the incidence of breast cancer in the United States increased a modest 8% among women under 50 years of age, while it rose 32.1% among women in the age group of 50 years or older (Reese et al., 1991). This upward shift is consistent with the historical pattern of accumulation of organochlorine insecticide residues (xenoestrogens) in the environment (Mussalo-Rauhamaa et al., 1990; Wolff et al., 1993; Davis et al., 1993). Breast cancer is also the second leading cause of cancer deaths in women and it is estimated that in 1998, there will be an additional 43,900 deaths due to breast cancer. Environmental estrogens or endocrine dismptors have been suggested to play a role in the etiology or promotion of breast cancer (Davis et al., 1993; Dewailly et al., 1994). Experimental evidence reveals that xenoestrogens affect estrogen production and metabolism and are among the risk factors that cause breast cancer (Nelson et al., 1978; Berthois et al., 1986; Henderson et al., 1993; Jobling et al., 1995; Dees et al., 1997). Most of the known risk factors for breast cancer, which at least account for 30% of cases (Henderson et al., 1993) are linked with total life-time exposure to reproductive chemicals such as estrogen and xenoesrrogens.

It appears evident that soft tissue cancer in mammals is increasing every year as a result of increased estrogen levels and increased exposure to environmental xenoestrogens. For example, the number of prescriptions of estrogen for women in menopause is rapidly increasing, presently estimated at 50,000,000 prescriptions annually in the United States alone. This increasing use of estrogen partially accounts for the higher risk of breast cancer in both young and middle-aged women. Estrogen is present in all mammals and is essential in women for reproductive organs such as ovary, uterus, breast, etc. In men, however, estrogen is required for sperm production and maturation. The abusive use of estrogen prescribed for women is at least partially responsible for the development of soft tissue cancers, especially breast cancer. It is therefore desirable to antagonize or counteract the adverse effects of estrogen in women.

The current FDA-approved treatments, e.g., tamoxifen, in the United States are effective to some extent in some of the female population in antagonizing the adverse effects of estrogen. Unfortunately, these treatments are not totally effective and may themselves cause additional health related effects, such as uterine cancer. Thus, if one could identify compounds that would make the current treatments more effective, or would work in conjunction with, or in lieu of, the present treatments, it is possible some of these adverse side effects would be alleviated or even eliminated. A possible source of alternative treatments are natural, non-toxic compounds. It is proposed that these compounds would advantageously provide for safer and more effective treatments.

The use of certain monoterpenoid plant essential oils (alpha-terpineol, linalool, and limonene) is suggested as a potential treatment for breast cancer. These monoterpenoids however are not totally effective and have been proven to be weak anti-proliferative cancer products. In addition, these data do not suggest the capability of these compounds to antagonize of action of estrogen. This may raise the question of how this product may interact in women with estrogen supplement.

Accordingly, there is a great need for novel pharmaceutical compositions containing non-toxic ingredients that may be effectively used in the prevention or treatment of soft tissue cancer in mammals.

SUMMARY OF THE INVENTION

A primary object of the present invention is to provide novel compositions that contain certain plant essential oils, natural or synthetic in source, or mixtures or derivatives thereof, as a prophylactic for, or a treatment of, soft tissue cancer.

The above and other objects are accomplished by the present invention which is directed to novel pharmaceutical compositions containing at least one plant essential oil compound, including mixtures or derivatives thereof, which are synthetically made or obtained from natural sources. The present invention is also directed to methods for using such novel pharmaceutical compositions for prophylactically or therapeutically treating soft tissue cancers.

Additional objects and attendant advantages of the present invention will be set forth, in part, in the description that follows, or may be learned from practicing or using the present invention. The objects and advantages may be realized and attained by means of the instrumentalities and combinations particularly recited in the appended claims. It is to be understood that the foregoing general description and the following detailed description are exemplary and explanatory only and are not to be viewed as being restrictive of the invention, as claimed.

DETAILED DESCRIPTION OF PREFERRED EMBODIMENTS

All patents, patent applications and literatures cited in this description are incorporated herein by reference in their entirety. In the case of inconsistencies, the present disclosure, including definitions, will prevail.

In a preferred embodiment, the present invention provides a novel pharmaceutical composition for preventing or treating cancer, the composition comprising at least one plant essential oil compound including mixtures or derivatives of plant essential oil compounds derived from either natural or synthetic sources.

The specific plant essential oils disclosed herein or derivative thereof comprise a monocyclic, carbocyclic ring structure having six-members and substituted by at least one oxygenated or hydroxyl functional moiety. Examples of plant essential oils encompassed within the present invention, include, but are not limited to, members selected from the group consisting of aldehyde C16 (pure), amyl cinnamic aldehyde, amyl salicylate, anisic aldehyde, benzyl alcohol, benzyl acetate, cinnamaldehyde, cinnamic alcohol, α-terpineol, carvacrol, carveol, citral, citronellal, citronellol, p-cymene, diethyl phthalate, dimethyl salicylate, dipropylene glycol, eucalyptol (cineole), eugenol, iso-eugenol, galaxolide, geraniol, guaiacol, ionone, d-limonene, menthol, methyl anthranilate, methyl ionone, methyl salicylate, α-phellandrene, pennyroyal oil perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, ethyl vanillin, and the like.

As plant essential oil compounds are known and used for other purposes, they may be prepared by a skilled artisan by employing known methods. In addition, they may be purchased from conventional sources, may be readily isolated from specific plants or trees and purified (isolated) or may be synthesized using conventional techniques. Advantageously, these compounds may be conveniently synthesized from readily available starting materials. The relative ease with which the compositions of the present invention can be synthesized represents an enormous advantage in the large-scale production of these compounds.

It will be appreciated that the therapeutically-active plant essential oil compounds of the present invention may be modified or derivatized by appending appropriate functionalities, i.e., functional groups, to enhance selective biological properties. Such modifications are known in the art and include those that increase biological penetration into a given biological compartment (e.g., blood, lymphatic system, central nervous system), increase oral availability, increase solubility to allow administration by injection, alter metabolism and alter rate of excretion. In addition, the plant essential oil compounds may be altered to pro-drug form such that the desired therapeutically-active form of the compound is created in the body of the patient as the result of the action of metabolic or other biochemical processes on the pro-drug. Some examples of pro-drug forms include ketal, acetal, oxime, and hydrazone forms of compounds which contain ketone or aldehyde groups.

Moreover, the therapeutically-effective plant essential oil compounds of the present invention may contain one or more asymmetric carbon atoms and thus may occur as racemates and racemic mixtures, single enantiomers, diastereomeric mixtures and individual diastereomers. Each stereogenic carbon may be of the R or S configuration. All such isomeric forms of these compounds are expressly included within the purview of the present invention.

As will be appreciated, the compositions and method of the present invention include pharmaceutical compositions that comprise at least one plant essential oil, and pharmaceutically acceptable salts thereof, in combination with any pharmaceutically acceptable carrier, adjuvant or vehicle. The term "pharmaceutically acceptable carrier or adjuvant" refers to a carrier or adjuvant that may be administered to a patient, together with a plant essential oil compound of the present invention, and which does not destroy the pharmacological activity thereof and is nontoxic when administered in doses sufficient to deliver a therapeutic amount of the compound.

Pharmaceutically acceptable salts of the plant essential oil compounds of this invention include those derived from pharmaceutically acceptable inorganic and organic acids and bases. Examples of suitable acid salts include, without limitation, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and N—($C_{1-4}$alkyl)4+ salts. The present invention also envisions the quaternization of any basic nitrogen-containing groups of the compounds disclosed herein. Water or oil-soluble or dispersible products may be obtained by such quaternization.

Further, pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d.alpha-tocopherol polyethyleneglycol 1000 succinate, or other similar polymeric delivery matrices or systems, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-beta-cyclodextrins, or other solublized derivatives may also be advantageously used to enhance delivery of therapeutically-effective plant essential oil compounds of the present invention.

The pharmaceutical compositions of this invention may be administered orally, parenterally, by inhalation spray, topically, rectally, nasally, buccally, vaginally or via an implanted reservoir, however, oral administration or administration by injection is preferred. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringers solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of the present invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of the present invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Although rare, topical administration of the pharmaceutical compositions of the present invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Another acceptable pharmaceutical preparation would be an encapsulated form of the plant essential oils, as is, or modified as per the prior descriptions. The walls of the capsules could be designed to release the plant essential oils rapidly, i.e. one minute, hour or day, or it could be designed to release over some designated period of time, i.e. days, weeks or months. The wall materials could be natural or synthetic polymers acceptable to the US FDA or composed of lipids or other suitable materials. These capsules could be delivered either orally or by injection and could be either water or oil based depending upon the desired method of use or required rate of release.

Dosage levels of between about 0.001 and about 100 mg/kg body weight per day, preferably between about 0.5 and about 75 mg/kg body weight per day of the active ingredient compound are useful in the prevention and treatment of soft tissue cancers. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

The prophylactic use of the present invention may require the daily intake of a prophylactically-effective amount.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of a cancer, the patient's disposition to cancer and the judgment of the treating physician.

The compositions and methods of the present invention will be further illustrated in the following, non-limiting Examples. The Examples are illustrative of various embodiments only and do not limit the claimed invention regarding the materials, conditions, weight ratios, process parameters and the like recited herein. When reading the following Examples, it will be appreciated that the growth and proliferation of MCF-7 cells are strictly estrogen-dependent. In the presence of estrogen, the cells grow, confluent and form foci, the landmark of tumor diagnosis. In the absence of estrogen, the growth of these cells is slow and the formation of foci is rare.

EXAMPLE 1

Antiproliferative Effect on Human Epithelial Breast Cancer Cells (MCF-7)

MCF-7 cells were cultured in growth medium supplemented with 10% fetal bovine serum (FBS). At 85% confluence, cells were sub-cultured in 5% FBS serum stripped medium, phenol red free for 24 hours prior to the treatment of the test chemical. After 24 hours of treatment cell proliferation was measured using $^3$H-thymidine incorporation. These test chemicals were tested in the presence and absence of estrogen to address if they have anti-estrogenic activity in addition to their antiproliferative effect. The study was done in triplicate and a control was used with solvent only. Control received solvent only at <0.1% ethanol. Estrogen was tested at 1 nM (=0.27 ng $E_2$/ml). Exemplary plant essential oil compounds were tested at 50 ug/ml. Results are shown in Table 1.

TABLE 1

| | $^3$H-thymidine incorporation | | |
|---|---|---|---|
| Test Chemical | dpm/ug protein | % of control value | % of estrogen value |
| Control | 414.2 | 100 | |
| Estrogen | 658.6 | 158 | 100 |
| α-terpineol | 480.5 | 116 | |
| α-terpineol + estrogen | 679.1 | 164 | 103 |
| Trans-anethole | 434.9 | 105 | |
| Trans-anethole + estrogen | 589.8 | 142 | 89 |
| Carvacrol | 207.2 | 50 | |
| Carvacrol + estrogen | 181.7 | 43 | 28 |
| Cinnamic alcohol | 18.5 | 4 | |
| Cinnamic alcohol + estrogen | 220.8 | 53 | 34 |
| Eugenol | 215.6 | 52 | |
| Eugenol + estrogen | 289.1 | 70 | 44 |
| Iso-eugenol | 119 | 29 | |
| Iso-eugenol + estrogen | 164 | 40 | 25 |
| Thymol | 97.3 | 23 | |
| Thymol + estrogen | 108.2 | 26 | 16 |
| Citronellal | 85.2 | 20 | |
| Citronellal + estrogen | 284.0 | 69 | 43 |
| p-cymene | 419.0 | 101 | |
| p-cymene + estrogen | 632.0 | 152 | 96 |
| Eucalyptol | 398.0 | 96 | |
| Eucalyptol + estrogen | 568.0 | 137 | 86 |
| Methyl salicylate | 444.0 | 107 | |
| Methyl salicylate + estrogen | 693.9 | 168 | 106 |

EXAMPLE 2

Antiproliferative Effect

MCF-7 cells were cultured in growth medium supplemented with 10% fetal bovine serum (FBS). At 85% confluence, cells were sub-cultured in 5% FBS serum stripped medium, phenol red free for 24 hours prior to the treatment of the test chemical. After 24 hours of treatment cell proliferation was measured using $^3$H-thymidine incorporation. These test chemicals were tested in the presence and absence of estrogen to address if they have anti-estrogenic activity in addition to their antiproliferative effect. The study was done in triplicate and a control was used with solvent only. Control received solvent only at <0.1% ethanol. Estrogen was tested at 1 nM (0.27 ng $E_2$/ml). Plant essential oil compounds were tested at 50 ug/ml. Results are shown Table 2.

TABLE 2

| | $^3$H-thymidine incorporation | | |
|---|---|---|---|
| Test Chemical | dpm/μg protein | % of control value | % of estrogen value |
| Control | 438.1 | 100 | |
| Estrogen | 664.2 | 151.6 | 100 |
| α-terpineol | 490.7 | 112.0 | |
| α-terpineol + estrogen | 636.7 | 145.3 | 96 |
| Guaiacol | 712.3 | 162.6 | |
| Guaiacol + estrogen | 788.8 | 180.1 | 119 |
| R-(+)-Limonene | 393.1 | 89.7 | |
| R-(+)-Limonene + estrogen | 522.6 | 119.3 | 79 |
| α-phellandrene | 348.4 | 79.5 | |
| α-phellandrene + estrogen | 635.3 | 145.0 | 96 |

EXAMPLE 3

Dose-Response Effect on $E_2$-Induced Cell Growth

MCF-7 cells were cultured in growth medium supplemented with 10% fetal bovine serum (FBS). At 85% confluence, cells were sub-cultured in 6 well petri-dishes and supplemented with 5% FBS serum stripped medium, phenol red free for 24 hours prior to the treatment of different concentrations of the test chemicals. After 5 days of treatment cells were trypsinized, collected using Eppendorf microcentrifuge. The cell pellets were resuspended in 1% trypan blue and three aliquots (10 ul each) of the viable cell suspension were counted using a haemocytometer assay. Each sample was then counted three times and the data shown is the average of three counts. These test chemicals were tested in the presence of 10 nM estrogen (=2.7 ng estrogen/ml). Two wells per test concentration were used. This experiment was repeated two times. Control received solvent only at <0.1% ethanol. Results are shown in Table 3.

TABLE 3

| | Cell count × $(10^4)$/ml | | | |
|---|---|---|---|---|
| Treatment | well #1 | well #2 | average | % of control |
| Day 5. | | | | |
| Control | 22 | 22 | 22.0 | 100 |
| $E_2$ (10 nM) | 36 | 28 | 32.0 | 145 |
| | | | | % anti-$E_2$ |
| $E_2$/thymol (20 μg/ml) | 10 | 14 | 12.0 | 62.50 |
| $E_2$/thymol (10 μg/ml) | 12 | 12 | 12.0 | 62.50 |
| $E_2$/thymol (5 μg/ml) | 20 | 18 | 19.0 | 40.60 |
| $E_2$/thymol (1 μg/ml) | 32 | 32 | 32.0 | 00.00 |
| $E_2$/isoeugenol (20 μg/ml) | 10 | 10 | 10.0 | 69.00 |
| $E_2$/isoeugenol (10 μg/ml) | 6 | 10 | 8.0 | 75.00 |
| $E_2$/isoeugenol (5 μg/ml) | 18 | 23 | 21.0 | 35.60 |
| $E_2$/isoeugenol (1 μg/ml) | 21 | 21 | 21.0 | 35.60 |
| $E_2$/eugenol (20 μg/ml) | 10 | 16 | 13.0 | 60.40 |
| $E_2$/eugenol (10 μg/ml) | 18 | 14 | 16.0 | 50.00 |
| $E_2$/eugenol (5 μg/ml) | 19 | 19 | 19.0 | 41.70 |
| $E_2$/eugenol (1 μg/ml) | 19 | 29 | 24.0 | 25.00 |
| $E_2$/benzyl alcohol (50 μg/ml) | 24 | 18 | 21.0 | 35.40 |
| $E_2$/cinnamic aldehyde (50 μg/ml) | 00 | 02 | 01.0 | 96.90 |

Our data show a dose-response relationship of plant essential oil compounds, and their antiestrogenicity against $E_2$-induced abnormal cell growth and proliferation in human epithelial breast cancer cells (MCF-7). These data demonstrated that thymol at low dose (5 ug/ml) provided 40% protection against the $E_2$-induced abnormal growth in cancer breast cells. In addition, these data also showed that eugenol (1 ug/ml) and isoeugenol (1 ug/ml) expressed 35% and 25% protection, respectively, against the $E_2$-induced abnormal growth in cancer breast cells (see example 3). Further, cinnamic aldehyde provided approximately 96% control against the $E_2$-induced abnormal growth in cancer breast cells at 50 ug/ml (see example 3).

The above Examples show, inter alia, that certain plant essential oils and combinations thereof are anti-proliferative, anti-estrogenic and/or anti-mitogenic compounds that are useful for prophylactically or therapeutically treating soft tissue cancers.

Although illustrative embodiments of the present invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A method for treating breast cancer, comprising administrating to a patient in need thereof a therapeutically effective amount of a composition comprising eugenol.

2. The method of claim 1, further comprising an acceptable carrier.

3. The method of claim 1, wherein the cancer is soft tissue cancer.

* * * * *